(12) United States Patent
Du et al.

(10) Patent No.: US 11,148,994 B2
(45) Date of Patent: Oct. 19, 2021

(54) PROCESS FOR MANUFACTURE OF 1,1,1-TRIFLUORO-2-CHLOROETHANE

(71) Applicant: Fujian Yongjing Technology Co., Ltd, Shaowu (CN)

(72) Inventors: Hongjun Du, Shaowu (CN); Wenting Wu, Shaowu (CN)

(*) Notice: Subject to any disclaimer, the term of this patent is extended or adjusted under 35 U.S.C. 154(b) by 0 days.

(21) Appl. No.: 16/907,185

(22) Filed: Jun. 20, 2020

(65) Prior Publication Data

US 2021/0017117 A1    Jan. 21, 2021

Related U.S. Application Data

(62) Division of application No. 16/517,547, filed on Jul. 20, 2019.

(51) Int. Cl.
| | |
|---|---|
| *C07C 209/08* | (2006.01) |
| *C07C 211/15* | (2006.01) |
| *B01J 27/06* | (2006.01) |

(52) U.S. Cl.
CPC .......... *C07C 209/08* (2013.01); *C07C 211/15* (2013.01); *B01J 27/06* (2013.01)

(58) Field of Classification Search
None
See application file for complete search history.

(56) References Cited

U.S. PATENT DOCUMENTS 5,623,092 A * 4/1997 Scott ................. B01J 23/26
570/168

FOREIGN PATENT DOCUMENTS

EP    0462514    * 12/1991

OTHER PUBLICATIONS

Yao et al. (Renewable and Sustainable Energy Reviews, 2015, 47, 519).*

* cited by examiner

*Primary Examiner* — Sudhakar Katakam
*Assistant Examiner* — Jennifer C Sawyer

(57) ABSTRACT

The invention relates to a new process for the manufacture of fluoroaryl compounds and derivatives thereof, in particular of fluorobenzenes and derivatives thereof, and especially wherein said manufacture relates to an environmentally friendly production of the said compounds. Thus, the present invention overcomes the disadvantages of the prior art processes, and in a surprisingly simple and beneficial manner, and as compared to the prior art processes, in particular, the invention provides a more efficient and energy saving processes, and also provides a more environmentally friendly process, for the manufacture of nuclear fluorinated aromatics, and preferably of nuclear fluorinated fluorobenzenes. Accordingly, in one aspect of the invention, an industrially beneficial process for preparing fluorobenzenes from halobenzene precursors using HF to form hydrogen halide is provided by the present invention. A beneficial and surprisingly simple use of chlorobenzene as an industrially interesting starting material in the manufacture of fluorobenzene is provided.

8 Claims, 1 Drawing Sheet

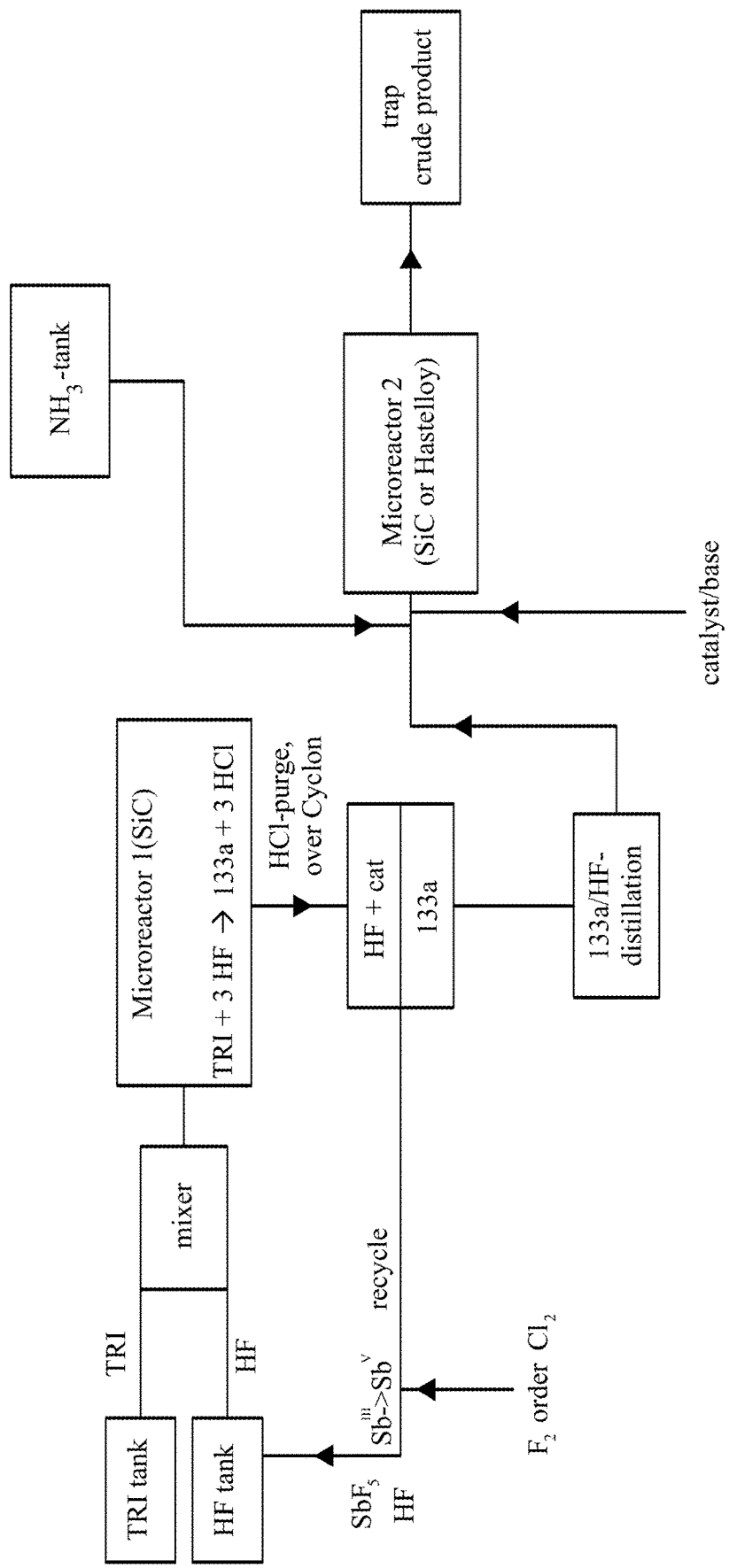

PROCESS FOR MANUFACTURE OF 1,1,1-TRIFLUORO-2-CHLOROETHANE

BACKGROUND OF THE INVENTION

Field of the Disclosure

The invention relates to a process for the manufacture of HCFC-133a (1,1,1-trifluoro-2-chloroethane (HCFC-133a). Especially, the invention relates to process for the manufacture of HCFC-133a (1,1,1-trifluoro-2-chloroethane), in particular by reacting trichloroethylene (TRI) as a starting material or intermediate material with HF in the presence of the catalyst.

Description of Related Art

All prior art processes for the manufacture of HCFC-133a (1,1,1-trifluoro-2-chloroethane (HCFC-133a) are based on PER (tetrachloroethylene) or TRI (trichloroethylene) as starting materials and are performed in gas-phase reactions.

Furthermore, the following two-step production methods for HCFC-133a ($CF_3CH_2Cl$, the most important intermediate in production of HFC-134a; $CF_3$—$CH_2F$) are known in conventional batch or continuous reactors from the International patent application WO 2000/076945 A2 (Braun et al.), and the Chinese patent application CN 103102241 A (Yang Huimin).

Herein, the WO 2000/076945 A2 discloses a method of UV-activated chlorination, whereby alkanes containing chlorine can be produced by attaching chlorine to C—C-double bonds or C—C-triple bonds or by exchanging hydrogen for chlorine, by bringing the starting compound in the gas or liquid phase into contact with elementary chlorine and irradiating them with UV light with a wavelength of lambda >280 nm. In this way, pentachloroethane ($CCl_3CHCl_2$) can be produced from trichloroethylene ($Cl_2C$=$CHCl$), CFC-113 from HCFC-123 or HFC-133a, CFC-112a from HCFC-142b or HCFC-123 from HCFC-133a. The method is also suitable for purifying HFC-365mfc (1,1,1,3,3-pentafluorobutane) with the aim of separating impurities that can be photochlorinated. The claimed advantages of the method are high yields and excellent selectivity. A reaction scheme for the manufacture of, for example, is as follows:

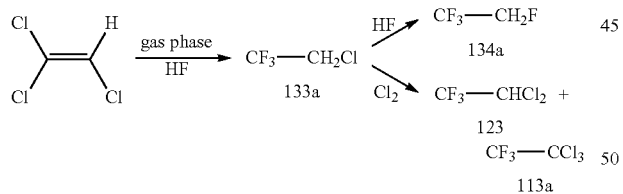

HCFC-133a (1,1,1-trifluoro-2-chloroethane (HCFC-133a) is already used industrially for producing as a precursor to the refrigerant 134a in a gas-phase reaction at a temperature of about 300° C. A disadvantage of a gas-phase reaction (even if the chemistry works well) is, of course, the high energy demand.

Object of the present invention is to overcome the disadvantages of the prior art processes, in particular to provide a more efficient and energy saving processes, also more environmentally friendly process, for the manufacture.

SUMMARY OF THE INVENTION

The objects of the invention are solved as defined in the claims, and described herein after in detail. In particular, the present invention employs in preferred embodiments one or more microreactors in the concerned processes of the invention, i.e. in a process for the manufacture of HCFC-133a (1,1,1-trifluoro-2-chloroethane) and/or the manufacture of TFEA (trifluoroethylamine) using HCFC-133a as a starting material, and/or the present invention employs in preferred embodiments one or more phase separation method.

The manufacture of trifluoroethylamine(TFEA) is best or shortest, respectively, done from CF3CH2Cl (HCFC-133a), i.e. 1,1,1-trifluoro-2-chloroethane.

Thus, the present invention relates to a process for the manufacture of trifluoroethylamine TFEA) which is prepared from HCFC-133a (1,1,1-trifluoro-2-chloroethane (HCFC-133a) by reacting with ammonia ($NH_3$) in a liquid phase reaction.

The invention also relates to a process for the manufacture of HCFC-133a (1,1,1-trifluoro-2-chloroethane (HCFC-133a) by reacting with hydrogene fluoride (HF) in a liquid phase reaction. The obtained HCFC-133a (1,1,1-trifluoro-2-chloroethane (HCFC-133a) serves as starting material for the manufacture of the before said trifluoroethylamine (TFEA).

Thereby, the present invention overcomes the disadvantages of the prior art, in particular the disadvantage of a gas-phase reaction (even if the chemistry works well) of the high energy demand that the liquid-phase reaction according to the present invention does not have in that it is a more efficient and energy saving processes, also more environmentally friendly process, for the manufacture of HCFC-133a (1,1,1-trifluoro-2-chloroethane (HCFC-133a), e.g., as a starting material, and/or for the manufacture of trifluoroethylamine (TFEA) from HCFC-133a as starting material. Purification by phase separation provides even more energetic benefits, in context of the invention.

All known processes to HCFC-133a are in gas phase. This invention is disclosing a process in liquid phase staring from trichloroethylene (TRI) in a "one continuously or batch wise operated pot" which might follow the reaction mechanism disclosed below in the reaction scheme. Liquid phase processes vs. gas phase processes consume much less energy. If this could be combined with a phase separation this is the most economic energy saving process. The 5-steps chemistry, if done continuously in a continuous flow reactor according to the invention, and in particular in a so called microreactor, further improvements regarding safety (waterfree HF) and industrial feasibility and economic and energy saving operating mode can be achieved.

Below the reaction scheme is shown for a continuous microreactor preparation of HCFC-133a followed by a combination with downstream chemistry to a fluorinated building block (intermediate) trifluoroethylamine. As for trifluorethylamine the HCFC-133a should be HF free, a distillation step is added to remove excess HF and to avoid formation of $NH_4F$ in the amination step.

In contrast to the prior art processes for the manufacture of HCFC-133a (1,1,1-trifluoro-2-chloroethane (HCFC-133a) which are based on PER (tetrachloroethylene) or TRI (trichloroethylene) as starting materials and are performed in gas-phase reactions, the present invention provides a new process in liquid phase, e.g. according to the following reaction scheme:

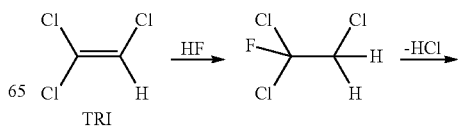

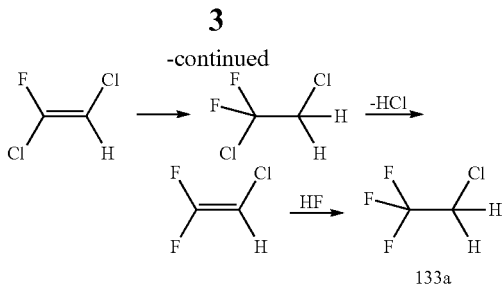

In a preferred embodiment, e.g. not intended to be limiting, the process is carried out in a microreactor. This applies to both, the manufacture of HCFC-133a (1,1,1-trifluoro-2-chloroethane (HCFC-133a) and the manufacture of trifluoroethylamine (TFEA) using HCFC-133a as a starting material.

In FIG. 1, shows an exemplary embodiment of a process scheme for the manufacture of HCFC-133a (1,1,1-trifluoro-2-chloroethane (HCFC-133a) and the manufacture of trifluoroethylamine (TFEA) using HCFC-133a as a starting material.

For example, the invention pertains to a method in which the production of HCFC-133a (1,1,1-trifluoro-2-chloroethane (HCFC-133a) and/or of trifluoroethylamine (TFEA), wherein at least one reaction step takes place in a microreactor. Particularly, in preferred embodiments of the invention pertains to a method in which the production of ofHCFC-133a (1,1,1-trifluoro-2-chloroethane (HCFC-133a) and/or of trifluoroethylamine (TFEA) wherein at least one reaction step takes place in a microreactor that is comprising or is made of SiC ("SiC-microreactor"), or in a microreactor that is comprising or is made of an alloy, e.g. such as Hastelloy C. In an embodiment, the processes for the manufacture of ofHCFC-133a (1,1,1-trifluoro-2-chloroethane (HCFC-133a) and/or of trifluoroethylamine (TFEA) can be efficiently combined in that HCFC-133a (1,1,1-trifluoro-2-chloroethane (HCFC-133a) produced by the method according the invention by using a microreactor, preferably a SiC-microreactor, may preferably advantageously serve as starting material/and/or intermediate material in the manufacture of trifluoroethylamine (TFEA), preferably also in a microreactor. In the said manufactures of HCFC-133a and/or for the manufacture of TFEA the HCFC-133a and/or the TEFA can be easily, e.g. by a method with only low energy consumption, purified and/or isolated, and preferably the process for purifying and/or isolating does not require a distillation. Advantageously, the separation from excess HF and from the catalyst can easily take place in an energy-saving manner by phase separation.

New processes comparable to the processes of the present invention, and their performing and reaction and/or purification and/or isolation conditions, which processes comparable are related to the manufacture of HCFC-122 (1,1,2-trichloro-2,2-difluoroethane) and of HCFC-123 (2,2-dichloro-1,1,1-trifluoroethane), are disclosed in the co-pending German patent application DE 10 2018 118 406.9 filed within the German Patent and Trademark Office on 30 Jul. 2018, which co-pending German patent application herein is incorporated by reference in its entirety. The person skilled in the field is capable to apply and/or modify the reaction and/or purification and/or isolation conditions disclosed in the co-pending German patent application in the context of HCFC-122 and/or HCFC-123, as appropriate to the present invention of manufacturing HCFC-133a and/or for the manufacture of TFEA the HCFC-133a.

In the processes according to the present invention in a preferred embodiment the invention is using a microreactor. But it is to be noted in a more general embodiment of the invention, apart from the said preferred embodiment of the invention that is using a microreactor, any other, e.g. preferentially pipe-like, continuous flow reactor with upper lateral dimensions of up to about 1 cm, and as defined herein, can be employed. Thus, such a continuous flow reactor preferably with upper lateral dimensions of up to about ≤5 mm, or of about ≤4 mm, refers to a preferred embodiment of the invention, e.g. preferably to amicroreactor.

In the before said embodiments of the present invention, the minimal lateral dimensions of the, e.g. preferentially pipe-like, continuous flow reactor can be about >5 mm; but is usually not exceeding about 1 cm. Thus, the lateral dimensions of the, e.g. preferentially pipe-like, continuous flow reactor can be in the range of from about >5 mm up to about 1 cm, and can be of any value therein between. For example, the lateral dimensions of the, e.g. preferentially pipe-like, continuous flow reactor can be about 5.1 mm, about 5.5 mm, about 6 mm, about 6.5 mm, about 7 mm, about 7.5 mm, about 8 mm, about 8.5 mm, about 9 mm, about 9.5 mm, and about 10 mm, or can be can be of any value intermediate between the said values.

In the before said embodiments of the present invention using a microreactor preferentially the minimal lateral dimensions of the microreactor can be at least about 0.25 mm, and preferably at least about 0.5 mm; but the maximum lateral dimensions of the microreactor does not exceed about ≤5 mm. Thus, the lateral dimensions of the, e.g. preferential microreactorcan be in the range of from about 0.25 mm up to about ≤5 mm, and preferably from about 0.5 mm up to about ≤5 mm, and can be of any value therein between. For example, the lateral dimensions of the preferential microreactorcan be about 0.25 mm, about 0.3 mm, about 0.35 mm, about 0.4 mm, about 0.45 mm, and about 5 mm, or can be can be of any value intermediate between the said values.

As stated here before in the embodiments of the present invention in its broadest meaning is employing, preferentially pipe-like, continuous flow reactor with upper lateral dimensions of up to about 1 cm. Such continuous flow reactor, for example is a plug flow reactor (PFR).

The plug flow reactor (PFR), sometimes called continuous tubular reactor, CTR, or piston flow reactors, is a reactor used to perform and describe chemical reactions in continuous, flowing systems of cylindrical geometry. The PFR reactor model is used to predict the behaviour of chemical reactors of such design, so that key reactor variables, such as the dimensions of the reactor, can be estimated.

Fluid going through a PFR may be modelled as flowing through the reactor as a series of infinitely thin coherent "plugs", each with a uniform composition, traveling in the axial direction of the reactor, with each plug having a different composition from the ones before and after it. The key assumption is that as a plug flows through a PFR, the fluid is perfectly mixed in the radial direction (i.e. in the lateral direction) but not in the axial direction (forwards or backwards).

Accordingly, the terms used herein to define the reactor type used in the context of the invention such like "continuous flow reactor", "plug flow reactor", "tubular reactor", "continuous flow reactor system", "plug flow reactor system", "tubular reactor system", "continuous flow system", "plug flow system", "tubular system" are synonymous to each other and interchangeably by each other.

The reactor or system may be arranged as a multitude of tubes, which may be, for example, linear, looped, meandering, circled, coiled, or combinations thereof. If coiled, for example, then the reactor or system is also called "coiled reactor" or "coiled system".

In the radial direction, i.e. in the lateral direction, such reactor or system may have an inner diameter or an inner cross-section dimension (i.e. radial dimension or lateral dimension, respectively) of up to about 1 cm. Thus, in an embodiment the lateral dimension of the reactor or system may be in the range of from about 0.25 mm up to about 1 cm, preferably of from about 0.5 mm up to about 1 cm, and more preferably of from about 1 mm up to about 1 cm.

In further embodiments the lateral dimension of the reactor or system may be in the range of from about >5 mm to about 1 cm, or of from about 5.1 mm to about 1 cm.

If the lateral dimension at maximum of up to about ≤5 mm, or of up to about ≤4 mm, then the reactor is called "microreactor". Thus, in still further microreactor embodiments the lateral dimension of the reactor or system may be in the range of from about 0.25 mm up to about ≤5 mm, preferably of from about 0.5 mm up to about ≤5 mm, and more preferably of from about 1 mm up to about ≤5 mm; or the lateral dimension of the reactor or system may be in the range of from about 0.25 mm up to about ≤4 mm, preferably of from about 0.5 mm up to about ≤4 mm, and more preferably of from about 1 mm up to about ≤4 mm.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIG. 1 shows an exemplary embodiment of a process scheme for the manufacture of HCFC-133a (1,1,1-trifluoro-2-chloroethane) and the manufacture of trifluoroethylamine (TFEA) using HCFC-133a as a starting material.

DESCRIPTION OF THE PREFERRED EMBODIMENTS

As to the term "microreactor": A "microreactor" or "microstructured reactor" or "microchannel reactor", in one embodiment of the invention, is a device in which chemical reactions take place in a confinement with typical lateral dimensions of about ≤5 mm, or of about ≤4 mm; an example of a typical form of such confinement are microchannels. Generally, in the context of the invention, the term "microreactor": A "microreactor" or "microstructured reactor" or "microchannel reactor", denotes a device in which chemical reactions take place in a confinement with typical lateral dimensions of, for example, about 5 mm.

Microreactors are studied in the field of micro process engineering, together with other devices (such as micro heat exchangers) in which physical processes occur. The microreactor is usually a continuous flow reactor (contrast with/to a batch reactor). Microreactors offer many advantages over conventional scale reactors, including vast improvements in energy efficiency, reaction speed and yield, safety, reliability, scalability, on-site/on-demand production, and a much finer degree of process control.

Microreactors are used in "flow chemistry" to perform chemical reactions.

In flow chemistry, wherein often microreactors are used, a chemical reaction is run in a continuously flowing stream rather than in batch production. Batch production is a technique used in manufacturing, in which the object in question is created stage by stage over a series of workstations, and different batches of products are made. Together with job production (one-off production) and mass production (flow production or continuous production) it is one of the three main production methods. In contrast, in flow chemistry the chemical reaction is run in a continuously flowing stream, wherein pumps move fluid into a tube, and where tubes join one another, the fluids contact one another. If these fluids are reactive, a reaction takes place. Flow chemistry is a well-established technique for use at a large scale when manufacturing large quantities of a given material. However, the term has only been coined recently for its application on a laboratory scale.

Continuous flow reactors, e.g. such as used as microreactor, are typically tube like and manufactured from non-reactive materials, such known in the prior art and depending on the specific purpose and nature of possibly aggressive agents and/or reactants. Mixing methods include diffusion alone, e.g. if the diameter of the reactor is narrow, e.g. of about ≤5 mm, or about ≤4 mm, such as in microreactors, and static mixers. Continuous flow reactors allow good control over reaction conditions including heat transfer, time and mixing. The residence time of the reagents in the reactor, i.e. the amount of time that the reaction is heated or cooled, is calculated from the volume of the reactor and the flow rate through it: Residence time=Reactor Volume/Flow Rate. Therefore, to achieve a longer residence time, reagents can be pumped more slowly and/or a larger volume reactor used. Production rates can vary from milliliters minute to liters per hour.

Some examples of flow reactors are spinning disk reactors (Colin Ramshaw); spinning tube reactors; multi-cell flow reactors; oscillatory flow reactors; microreactors; hex reactors; and aspirator reactors. In an aspirator reactor a pump propels one reagent, which causes a reactant to be sucked in. Also to be mentioned are plug flow reactors and tubular flow reactors.

In the present invention, in one embodiment it is particularly preferred to employ a microreactor.

In an alternative embodiment of the invention, it is also optionally desired to employ another continuous flow reactor than a microreactor, preferably if, for example, the (halogenation promoting, e.g. the halogenation or preferably the halogenation) catalyst composition used in the halogenation or fluorination tends to get viscous during reaction or is viscous already as a said catalyst as such. In such case, a continuous flow reactor, i.e. a device in which chemical reactions take place in a confinement with lower lateral dimensions of greater than that indicated above for a microreactor, i.e. of greater than about 1 mm, but wherein the upper lateral dimensions are about ≤5 mm, or about ≤4 mm. Accordingly, in this alternative embodiment of the invention, employing a continuous flow reactor, the term "continuous flow reactor" preferably denotes a device in which chemical reactions take place in a confinement with typical lateral dimensions of from about ≥0.25 mm up to about ≤5 mm, or up to about ≤4 mm, preferably of from about ≥0.5 mm up to about ≤5 mm, or up to about ≤4 mm, kore preferably of from about ≥1 mm up to about ≤5 mm, or up to about ≤4 mm. In such an embodiment of the invention it is particularly preferred to employ as a continuous flow reactor a plug flow reactor and/or a tubular flow reactor, with the said lateral dimensions. Also, in such an embodiment of the invention, as compared to the embodiment employing a microreactor, it is particularly preferred to employ higher flow rates in the continuous flow reactor, preferably in the plug flow reactor and/or a tubular flow reactor, with the said lateral dimensions. For example, such higher flow rates, are up to about 2 times higher, up to about 3 times higher, up to about 4 times higher, up to about 5 times higher, up to about 6 times higher, up to about 7 times higher, or any intermediate flow rate of from about ≥1 up to about ≤7 times higher, of from about ≥1 up to about ≤6 times higher, of from about ≥1 up to about ≤5 times higher, of from about ≥1 up to about ≤4 times higher, of from about ≥1 up to about ≤3 times higher, or of from about ≥1 up to about ≤2 times higher, each as compared to the typical flow rates indicated herein for a microreactor. Preferably, the said continuous flow reactor, more preferably the plug flow reactor and/or a tubular flow reactor, employed in this embodiment of the invention is configured with the construction materials as defined herein for the microreactors. For example, such construction materials are silicium carbide (SiC) and/or are alloys such as a highly corrosion resistant nickel-chromium-molybdenum-tungsten alloy, e.g. Hastelloy®, as described herein for the microreactors.

A very particular advantage of the present invention employing a microreactor, or a continuous flow reactor with the before said lateral dimensions, the number of separating steps can be reduced and simplified, and may be devoid of time and energy consuming, e.g. intermediate, distillation steps. Especially, it is a particular advantage of the present invention employing a microreactor, or a continuous flow reactor with the before said lateral dimensions, that for separating simply phase separation methods can be employed, and the non-consumed reaction components may be recycled into the process, or otherwise be used as a product itself, as applicable or desired.

In addition to the preferred embodiments of the present invention using a microreactor in steps (d) and (e), as defined herein and in the claims, in the processes according to the invention, in addition or alternatively to using a microreactor, it is also possible to use in steps (d) and (e) to employ a plug flow reactor or a tubular flow reactor, respectively.

Plug flow reactor or tubular flow reactor, respectively, and their operation conditions, are well known to those skilled in the field.

Although the use of a continuous flow reactor with upper lateral dimensions of about ≤5 mm, or of about ≤4 mm, and in particular of a microreactor, is particularly preferred in the present invention, depending on the circumstances, it could be imagined that somebody dispenses with an microreactor, then of course with yield losses and higher residence time, higher temperature, and instead takes a plug flow reactor or turbulent flow reactor, respectively. However, this could have a potential advantage, taking note of the mentioned possibly disadvantageous yield losses, namely the advantage that the probability of possible blockages (tar particle formation by non-ideal driving style) could be reduced because the diameters of the tubes or channels of a plug flow reactor are greater than those of a microreactor.

The possibly allegeable disadvantage of this variant using a plug flow reactor or a tubular flow reactor, however, may also be seen only as subjective point of view, but on the other hand under certain process constraints in a region or at a production facility may still be appropriate, and loss of yields be considered of less importance or even being acceptable in view of other advantages or avoidance of constraints.

In the following, the invention is more particularly described in the context of using a microreactor. Preferentially, a microreactor used according to the invention is a ceramic continuous flow reactor, more preferably a SiC (silicon carbide) continuous flow reactor, and can be used for material production at a multi-to scale. Within integrated heat exchangers and SiC materials of construction, it gives optimal control of challenging flow chemistry application. The compact, modular construction of the flow production reactor enables, advantageously for: long term flexibility towards different process types; access to a range of production volumes (5 to 400 l/h); intensified chemical production where space is limited; unrivalled chemical compatibility and thermal control.

Ceramic (SiC) microreactors, are e.g. advantageously diffusion bonded 3M SiC reactors, especially braze and metal free, provide for excellent heat and mass transfer, superior chemical compatibility, of FDA certified materials of construction, or of other drug regulatory authority (e.g. EMA) certified materials of construction. Silicon carbide (SiC), also known as carborundum, is a containing silicon and carbon, and is well known to those skilled in the art. For example, synthetic SiC powder is been mass-produced and processed for many technical applications.

For example, in the embodiments of the invention the objects are achieved by a method in which at least one reaction step takes place in a microreactor. Particularly, in preferred embodiments of the invention the objects are achieved by a method in which the production in at least one reaction step takes place in a microreactor that is comprising or is made of SiC ("SiC-microreactor"), or in a microreactor that is comprising or is made of an alloy, e.g. such as Hastelloy C, as it is each defined herein after in more detail.

Thus, without being limited to, for example, in an embodiment of the invention the microreactor suitable for, preferably for industrial, production an "SiC-microreactor" that is comprising or is made of SiC (silicium carbide; e.g. SiC as offered by Dow Corning as Type G1SiC or by Chemtrix MR555 Plantrix), e.g. providing a production capacity of from about 5 up to about 400 kg per hour; or without being limited to, for example, in another embodiment of the invention the microreactor suitable for industrial production is comprising or is made of Hastelloy C, as offered by Ehrfeld. Such microreactors are particularly suitable for the, preferably industrial, production.

In order to meet both the mechanical and chemical demands placed on production scale flow reactors, Plantrix modules are fabricated from 3M™SiC (Grade C). Produced using the patented 3M (EP 1 637 271 B1 and foreign patents) diffusion bonding technology, the resulting monolithic reactors are hermetically sealed and are free from welding lines/joints and brazing agents. More technical information on the Chemtrix MR555 Plantrix can be found in the brochure "CHEMTRIX—Scalable Flow Chemistry—Technical Information Plantrix® MR555 Series, published by Chemtrix BV in 2017, which technical information is incorporated herein by reference in its entirety.

Apart from the before said example, in other embodiments of the invention, in general SiC from other manufactures, and as known to the skilled person, of course can be employed in the present invention.

Accordingly, in the present invention as microreactor also the Protrix® of by Chemtrix can be used. Protrix® is a modular, continuous flow reactor fabricated from 3M® silicon carbide, offering superior chemical resistance and heat transfer. In order to meet both the mechanical and chemical demands placed on flow reactors, Protrix® modules are fabricated from 3M® SiC (Grade C). Produced using the patented 3M (EP 1 637 271 B1 and foreign patents) diffusion bonding technology, the resulting monolithic reactors are hermetically sealed and are free from welding lines/joints and brazing agents. This fabrication technique is a production method that gives solid SiC reactors (thermal expansion coefficient=$4.1 \times 10^{-6} K^{-1}$).

Designed for flow rates ranging from 0.2 to 20 ml/min and pressures up to 25 bar, Protrix® allows the user to develop continuous flow processes at the lab-scale, later transitioning to Plantrix® MR555 (×340 scale factor) for material production. The Protrix® reactor is a unique flow reactor with the following advantages: diffusion bonded 3M® SiC modules with integrated heat exchangers that offer unrivaled thermal control and superior chemical resistance; safe employment of extreme reaction conditions on a g scale in a standard fumehood; efficient, flexible production in terms of number of reagent inputs, capacity or reaction time. The general specifications for the Protrix® flow reactors are summarized as follows; possible reaction types are, e.g. A+B→P1+Q (or C)→P, wherein the terms "A", "B" and "C" represent educts, "P" and "P1" products, and "Q" quencher; throughput (ml/min) of from about 0.2 up to about 20; channel dimensions (mm) of 1×1 (pre-heat and mixer zone), 1.4×1.4 (residence channel); reagent feeds of 1 to 3; module dimensions (width×height) (mm) of 110×260; frame dimensions (width×height×length) (mm) approximately 400×300× 250; number of modules/frame is one (minimum) up to four (max.). More technical information on the ChemtrixProtrix® reactor can be found in the brochure "CHEMTRIX— Scalable Flow Chemistry—Technical Information Protrix®, published by Chemtrix BV in 2017, which technical information is incorporated herein by reference in its entirety.

The Dow Corning as Type G1SiC microreactor, which is scalable for industrial production, and as well suitable for process development and small production can be characterized in terms of dimensions as follows: typical reactor size (length×width×height) of 88 cm×38 cm×72 cm; typical fluidic module size of 188 mm×162 mm. The features of the Dow Corning as Type G1SiC microreactor can be summarized as follows: outstanding mixing and heat exchange: patented HEART design; small internal volume; high residence time; highly flexible and multipurpose; high chemical durability which makes it suitable for high pH compounds and especially hydrofluoric acid; hybrid glass/SiC solution for construction material; seamless scale-up with other advanced-flow reactors. Typical specifications of the Dow Corning as Type G1SiC microreactor are as follows: flow rate of from about 30 ml/min up to about 200 ml/min; operating temperature in the range of from about −60° C. up to about 200° C., operating pressure up to about 18 barg ("barg" is a unit of gauge pressure, i.e. pressure in bars above ambient or atmospheric pressure); materials used are silicon carbide, PFA (perfluoroalkoxy alkanes), perfluoroelastomer; fluidic module of 10 ml internal volume; options: regulatory authority certifications, e.g. FDA or EMA, respectively.

The reactor configuration of Dow Corning as Type G1SiC microreactor is characterized as multipurpose and configuration can be customized. Injection points may be added anywhere on the said reactor.

Hastelloy® C is an alloy represented by the formula NiCr21Mo14W, alternatively also known as "alloy 22" or "Hastelloy® C-22. The said alloy is well known as a highly corrosion resistant nickel-chromium-molybdenum-tungsten alloy and has excellent resistance to oxidizing reducing and mixed acids. The said alloy is used in flue gas desulphurization plants, in the chemical industry, environmental protection systems, waste incineration plants, sewage plants. Apart from the before said example, in other embodiments of the invention, in general nickel-chromium-molybdenum-tungsten alloy from other manufactures, and as known to the skilled person, of course can be employed in the present invention. A typical chemical composition (all in weight-%) of such nickel-chromium-molybdenum-tungsten alloy is, each percentage based on the total alloy composition as 100%: Ni (nickel) as the main component (balance) of at least about 51.0%, e.g. in a range of from about 51.0% to about 63.0%; Cr (chromium) in a range of from about 20.0 to about 22.5%, Mo (molybdenum) in a range of from about 12.5 to about 14.5%, W (tungsten or wolfram, respectively) in a range of from about 2.5 to about 3.5%; and Fe (iron) in an amount of up to about 6.0%, e.g. in a range of from about 1.0% to about 6.0%, preferably in a range of from about 1.5% to about 6.0%, more preferably in a range of from about 2.0% to about 6.0%. Optionally, the percentage based on the total alloy composition as 100%, Co (cobalt) can be present in the alloy in an amount of up to about 2.5%, e.g. in a range of from about 0.1% to about 2.5%. Optionally, the percentage based on the total alloy composition as 100%, V (vanadium) can be present in the alloy in an amount of up to about 0.35%, e.g. in a range of from about 0.1% to about 0.35%. Also, the percentage based on the total alloy composition as 100%, optionally low amounts (i.e. ≤0.1%) of other element traces, e.g. independently of C (carbon), Si (silicon), Mn (manganese), P (phosphor), and/or S (sulfur). In such case of low amounts (i.e. ≤0.1%) of other elements, the said elements e.g. of C (carbon), Si (silicon), Mn (manganese), P (phosphor), and/or S (sulfur), the percentage based on the total alloy composition as 100%, each independently can be present in an amount of up to about 0.1%, e.g. each independently in a range of from about 0.01 to about 0.1%, preferably each independently in an amount of up to about 0.08%, e.g. each independently in a range of from about 0.01 to about 0.08%. For example, said elements e.g. of C (carbon), Si (silicon), Mn (manganese), P (phosphor), and/or S (sulfur), the percentage based on the total alloy composition as 100%, each independently can be present in an amount of, each value as an about value: C≤0.01%, Si≤0.08%, Mn≤0.05%, P≤0.015%, S≤0.02%. Normally, no traceable amounts of any of the following elements are found in the alloy compositions indicated above: Nb (niobium), Ti (titanium), Al (aluminum), Cu (copper), N (nitrogen), and Ce (cerium).

Hastelloy® C-276 alloy was the first wrought, nickel-chromium-molybdenum material to alleviate concerns over welding (by virtue of extremely low carbon and silicon contents). As such, it was widely accepted in the chemical process and associated industries, and now has a 50-year-old track record of proven performance in a vast number of corrosive chemicals. Like other nickel alloys, it is ductile, easy to form and weld, and possesses exceptional resistance to stress corrosion cracking in chloride-bearing solutions (a form of degradation to which the austenitic stainless steels are prone). With its high chromium and molybdenum contents, it is able to withstand both oxidizing and non-oxidizing acids, and exhibits outstanding resistance to pitting and crevice attack in the presence of chlorides and other halides. The nominal composition in weight-% is, based on the total composition as 100%: Ni (nickel) 57% (balance); Co (cobalt) 2.5% (max.); Cr (chromium) 16%; Mo (molybdenum) 16%; Fe (iron) 5%; W (tungsten or wolfram, respectively) 4%; further components in lower amounts can be Mn (manganese) up to 1% (max.); V (vanadium) up to 0.35%

(max.); Si (silicon) up to 0.08% (max.); C (carbon) 0.01 (max.); Cu (copper) up to 0.5% (max.).

In another embodiments of the invention, without being limited to, for example, the microreactor suitable for the said production, preferably for the said industrial production, is an SiC-microreactor that is comprising or is made only of SiC as the construction material (silicium carbide; e.g. SiC as offered by Dow Corning as Type G1SiC or by Chemtrix MR555 Plantrix), e.g. providing a production capacity of from about 5 up to about 400 kg per hour.

It is of course possible according to the invention to use one or more microreactors, preferably one or more SiC-microreactors, in the production, preferably in the industrial production. If more than one microreactor, preferably more than one SiC-microreactors, are used in the production, preferably in the industrial production, then these microreactors, preferably these SiC-microreactors, can be used in parallel and/or subsequent arrangements. For example, two, three, four, or more microreactors, preferably two, three, four, or more SiC-microreactors, can be used in parallel and/or subsequent arrangements.

For laboratory search, e.g. on applicable reaction and/or upscaling conditions, without being limited to, for example, as a microreactor the reactor type Plantrix of the company Chemtrix is suitable.

For example, an industrial flow reactor ("IFR", e.g. Plantrix® MR555) comprises of SiC modules (e.g. 3M® SiC) housed within a (non-wetted) stainless steel frame, through which connection of feed lines and service media are made using standard Swagelok fittings. The process fluids are heated or cooled within the modules using integrated heat exchangers, when used in conjunction with a service medium (thermal fluid or steam), and reacted in zig-zag or double zig-zag, meso-channel structures that are designed to give plug flow and have a high heat exchange capacity. A basic IFR (e.g. Plantrix® MR555) system comprises of one SiC module (e.g. 3M® SiC), a mixer ("MRX") that affords access to A+B→P type reactions. Increasing the number of modules leads to increased reaction times and/or system productivity. The addition of a quench Q/C module extends reaction types to A+B→P1+Q (or C) P and a blanking plate gives two temperature zones. Herein the terms "A", "B" and "C" represent educts, "P" and "P1" products, and "Q" quencher.

Typical dimensions of an industrial flow reactor ("IFR", e.g. Plantrix® MR555) are, for example: channel dimensions in (mm) of 4×4 ("MRX", mixer) and 5×5 (MRH-I/MRH-II; "MRH" denotes residence module); module dimensions (width×height) of 200 mm×555 mm; frame dimensions (width×height) of 322 mm×811 mm. A typical throughput of an industrial flow reactor ("IFR", e.g. Plantrix® MR555) is, for example, in the range of from about 50 l/h to about 400 l/h. in addition, depending on fluid properties and process conditions used, the throughput of an industrial flow reactor ("IFR", e.g. Plantrix® MR555), for example, can also be >400 l/h. The residence modules can be placed in series in order to deliver the required reaction volume or productivity. The number of modules that can be placed in series depends on the fluid properties and targeted flow rate.

Typical operating or process conditions of an industrial flow reactor ("IFR", e.g. Plantrix® MR555) are, for example: temperature range of from about −30° C. to about 200° C.; temperature difference (service−process)<70° C.; reagent feeds of 1 to 3; maximum operating pressure (service fluid) of about 5 bar at a temperature of about 200° C.; maximum operating pressure (process fluid) of about 25 bar at a temperature of about ≤200° C.

The processes of the invention employ a halogenation catalyst, preferably a fluorination catalyst. Halogenation is a chemical reaction that involves the addition of one or more halogens to a compound or material. The pathway and stoichiometry of halogenation depends on the structural features and functional groups of the organic substrate, as well as on the specific halogen. Inorganic compounds such as metals also undergo halogenation. Fluorination is a halogenation wherein F (fluorine) is the halogen introduced into a compound or material. Halogenation and/or fluorination are well known to those skilled in the art, as well as the halogenation catalysts and/or fluorination catalysts involved in these reactions. For example, the addition of halogens, e.g. chlorine and/or fluorine, to alkenes proceeds via intermediate halonium ions as an active species, wherein "halonium ion" in organic chemistry denotes any onium compound (ion) containing a halogen atom, e.g. herein in context of the invention a fluorine atom, carrying a positive charge.

Halogenation catalysts and/or fluorination catalysts are well known to those skilled in the field, and preferably in context of the invention, based on Sb, As, Bi, Al, Zn, Fe, Mg, Cr, Ru, Sn, Ti, Co, Ni, preferably on the basis of Sb. More preferably a fluorination catalyst, especially an Sb fluorination catalysts providing the active species $H_2F+SbF^{6-}$.

In a first embodiment (1), the invention relates to a process for the manufacture of TFEA (trifluoroethylamine) comprising the steps of:

(a) providing HCFC-133a (1,1,1-trifluoro-2-chloroethane) as a starting material or intermediate material;

(b) providing $NH_3$ (ammonia) and a catalyst and/or a base;

(c) mixing the HCFC-133a of (a) with the HF and the catalyst of (b);

(d) feeding the mixture obtained in (c) into at least one continuous flow reactor with upper lateral dimensions of about ≤4 mm, preferably into at least one microreactor, and therein carrying out the reaction of HCFC-133a with $NH_3$ in the presence of the said catalyst to obtain a reaction mixture comprising TFEA;

preferably into at least one microreactor under one or more of the following conditions:
flow rate: of from about 10 ml/h up to about 400 l/h;
temperature: of from about 30° C. up to about 150° C.;
pressure: of from about 5 bar up to about 50 bar;
residence time: of from about 1 second, preferably from about 1 minute, up to about 60 minutes;

(e) withdrawing the reaction mixture obtained in (d) from the said continuous flow reactor, preferably from the microreactor, to yield a TFEA comprising product preferably a TFEA product; and (f) optionally purifying and/or isolating the TFEA product obtained in (e) to yield purified and/or isolated TFEA.

In a second embodiment (2), the invention relates to a process for the manufacture of HCFC-133a (1,1,1-trifluoro-2-chloroethane) comprising the steps of:

(a) providing TRI (trichloroethylene) as a starting material;

(b) providing HF (hydrogen fluoride) and a catalyst, preferably a halogenation promoting catalyst, more preferably fluorination promoting catalyst;

(c) mixing the TRI of (a) with the HF and the said catalyst of (b);

(d) feeding the mixture obtained in (c) into at least one continuous flow reactor with upper lateral dimensions of about ≤5 mm, or of about ≤4 mm, preferably into at least one microreactor, and therein carrying out the reaction of TRI with HF in the presence of the catalyst to obtain a reaction mixture comprising HCFC-133a;

preferably into at least one microreactor under one or more of the following conditions:
flow rate: of from about 10 ml/h up to about 400 l/h;
temperature: of from about 30° C. up to about 150° C.;
pressure: of from about 5 bar up to about 50 bar;
residence time: of from about 1 second, preferably from about 1 minute, up to about 60 minutes;

(e) withdrawing the reaction mixture obtained in (d) from the said continuous flow reactor, preferably from the microreactor, to yield a HCFC-133a comprising product, preferably a HCFC-133a product; and (f) optionally purifying and/or isolating the HCFC-133a product obtained in (e) to yield purified and/or isolated HCFC-133a.

In a third embodiment (3), the invention relates to a process for the manufacture of TFEA (trifluoroethylamine) according to embodiment (1), wherein in the step (a) the HCFC-133a (1,1,1-trifluoro-2-chloroethane) provided as a starting material or intermediate material is obtained by a process for the manufacture of HCFC-133a (1,1,1-trifluoro-2-chloroethane) as defined in embodiment (2).

In a fourth embodiment (4), the invention relates to a process for the manufacture of HCFC-133a (1,1,1-trifluoro-2-chloroethane) according to embodiment (1), or process for the manufacture of TFEA (trifluoroethylamine) according to embodiment (2), wherein at least one of the said continuous flow reactors, preferably at least one of the microreactors, in step (d) independently is a SiC-continuous flow reactor, preferably independently is a SiC-microreactor.

In a fifth embodiment (5), the invention relates to a process for the manufacture of HCFC-133a (1,1,1-trifluoro-2-chloroethane) according to embodiment (4), wherein the at least one of the microreactors in step (d) independently is a SiC-microreactor, preferably wherein the at least one of the microreactors, in step (d) is a SiC-microreactor in the step (d) as defined in embodiment (1).

In a sixth embodiment (6), the invention relates to a process according to any one of the embodiments (1) to (5), wherein in the fluorination reaction the catalyst is a halogenation catalyst, preferably a fluorination catalyst, on the basis of Sb, As, Bi, Al, Zn, Fe, Mg, Cr, Ru, Sn, Ti, Co, Ni, preferably on the basis of Sb, more preferably a fluorination catalyst wherein the fluorination catalyst is selected from the group consisting of Sb fluorination catalysts providing the active species $H_2F^+SbF_6^-$.

In a seventh embodiment (7), the invention relates to a process according to embodiment (6), wherein in the fluorination reaction the halogenation catalyst is antimony pentachloride and/or antimony pentafluoride, preferably wherein the catalyst is antimony pentafluoride ($SbF_5$) and is prepared in an autoclave by reaction of $SbCl_5$ with HF, more preferably consisting of $SbF_5$ in HF which forms the active species $H_2F^+SbF_6^-$, prior to reaction step (d) in the process according to any one of embodiments (1) to (3).

In an eights embodiment (8), the invention relates to a process according to any one of the preceding embodiments (1) to (7), wherein the process comprises in step (f) purifying and/or isolating the HCFC-133a product obtained in (e) as defined in embodiment (2) to yield purified and/or isolated HCFC-133a, and/or wherein the process comprises in step (f) purifying and/or isolating the TFEA product obtained in (e) as defined in embodiment (1) to yield purified and/or isolated TFEA;

preferably wherein in the process as defined in embodiment (2), the HCFC-133a (1,1,1-trifluoro-2-chloroethane) provided as a starting material or intermediate material which is obtained by a process for the manufacture of HCFC-133a (1,1,1-trifluoro-2-chloroethane) as defined in embodiment (2), and which is subjected in step (f) to purifying and/or isolating the HCFC-133a product obtained in (e) as defined in embodiment (2) to yield purified and/or isolated HCFC-133a as a starting material or intermediate material for the manufacture of TFEA (trifluoroethylamine) as defined in embodiment (1).

In an ninth embodiment (9), the invention relates to a process according to embodiment (8), wherein in step (f) as defined in any one of embodiments (1) or (2), the purifying and/or isolating of HCFC-133a and/or of the TFEA comprises or consists of a phase separation method, preferably wherein either at least or solely the purifying and/or isolating of HCFC-133a as defined in step (f) of embodiment (2) comprises or consists of a phase separation method.

In an tenth embodiment (10), the invention relates to a process according any one of the preceding embodiments (1) to (9), wherein at least in step (f) as defined in embodiment (2) for the purifying and/or isolating of HCFC-133a does not comprise a distillation to yield purified and/or isolated HCFC-133a, preferably when the purified and/or isolated HCFC-133a is provided to be used in a process for the manufacture of TFEA (trifluoroethylamine) as defined in embodiment (1), and wherein in the step (a) the HCFC-133a (1,1,1-trifluoro-2-chloroethane) provided as a starting material or intermediate material is obtained by a process for the manufacture of HCFC-133a (1,1,1-trifluoro-2-chloroethane) as defined in embodiment (2).

Finally, the present invention also pertains to a continuous flow two-step process for the manufacture of TFEA (trifluoroethylamine, wherein the HCFC-133a (1,1,1-trifluoro-2-chloroethane) provided as a starting material or intermediate material is obtained by a first continuous flow process step, and the HCFC-133a (1,1,1-trifluoro-2-chloroethane) obtained from the first continuous flow process step is reacted with HF in the presence of the a catalyst, e.g. a halogenation promoting catalyst, preferably a fluorination promoting catalyst, in a second continuous flow process step to obtain a reaction mixture comprising TFEA, withdrawing the said reaction mixture from the said second continuous flow process step to yield a TFEA comprising product, preferably a TFEA product, more preferably a product essentially comprising or consisting of TFEA; and optionally purifying and/or isolating the TFEA product obtained to yield purified and/or isolated TFEA. Such a continuous flow two-step process for the manufacture of TFEA (trifluoroethylamine) according to the invention preferably comprises a purification and/or separation step, wherein the said HCFC-133a (1,1,1-trifluoro-2-chloroethane) obtained by the said first continuous flow process step, prior to its use as a starting material or intermediate material for the manufacture of TFEA (trifluoroethylamine) in the second continuous flow process step, is subjected to purifying and/or separating to yield a purified and/or separated HCFC-133a product as a starting material or intermediate material for the said second continuous flow process step. More preferably the said purification and/or separation step to yield purified and/or separated HCFC-133a is a phase separation method.

Accordingly, in one embodiment, the invention pertains to a continuous flow two-step process for the manufacture of TFEA (trifluoroethylamine) using HCFC-133a (1,1,1-trifluoro-2-chloroethane) as intermediate starting material, comprising the steps of:

(i) providing HCFC-133a (1,1,1-trifluoro-2-chloroethane) as a starting material or intermediate material by a first continuous flow two-step process comprising the steps of:
  (a) providing TRI (trichloroethylene) as a starting material;
  (b) providing HF (hydrogen fluoride) and a catalyst, preferably a halogenation promoting catalyst, more preferably fluorination promoting catalyst;
  (c) mixing the TRI of (a) with the HF and the said catalyst of (b);
  (d) feeding the mixture obtained in (c) into at least one continuous flow reactor with upper lateral dimensions of about ≤5 mm, or of about ≤4 mm, preferably into at least one microreactor, and therein carrying out the reaction of TRI with HF in the presence of the catalyst to obtain a reaction mixture comprising HCFC-133a; most preferably into at least one microreactor under one or more of the following conditions:
    flow rate: of from about 10 ml/h up to about 400 l/h;
    temperature: of from about 30° C. up to about 150° C.;
    pressure: of from about 5 bar up to about 50 bar;
    residence time: of from about 1 second, preferably from about 1 minute, up to about 60 minutes;
  (e) withdrawing the reaction mixture obtained in (d) from the said first continuous flow reactor, most preferably from the said first microreactor, to yield a HCFC-133a comprising product, preferably a HCFC-133a product, more preferably a product essentially comprising or consisting of HCFC-133a; and (ii) optionally purifying and/or separating the said HCFC-133a product obtained in (e) to yield purified and/or separated HCFC-133a, preferably wherein the said purification and/or separation step to yield purified and/or separated HCFC-133a is a phase separation method;

(iii) providing NH₃ (ammonia) and a catalyst and/or a base;

(iv) mixing the HCFC-133a of step (i), optionally mixing the HCFC-133a of step (ii), with the NH₃ (ammonia) and a catalyst and/or a base of (iii);

(v) feeding the mixture obtained in (iv) into at least one second continuous flow reactor, most preferably into at least one microreactor, and therein carrying out the reaction of HCFC-133a with NH₃ (ammonia) in the presence of the said catalyst and/or a base to obtain a reaction mixture comprising TFEA;
  preferably into at least one second microreactor under one or more of the following conditions:
  preferably into at least one microreactor under one or more of the following conditions:
    flow rate: of from about 10 ml/h up to about 400 l/h;
    temperature: of from about 30° C. up to about 150° C.;
    pressure: of from about 5 bar up to about 50 bar;
    residence time: of from about 1 second, preferably from about 1 minute, up to about 60 minutes;

(vi) withdrawing the reaction mixture obtained in (v) from the said second continuous flow reactor, most preferably from the said second microreactor, to yield a TFEA comprising product, preferably a TFEA product, more preferably a product essentially comprising or consisting of the TFEA; and (vii) optionally purifying and/or isolating the TFEA product obtained in (vi) to yield purified and/or isolated TFEA.

In the preferred said continuous flow two-step process for the manufacture of TFEA (trifluoroethylamine) via HCFC-133a (1,1,1-trifluoro-2-chloroethane), independently the continuous flow reactor in the first and/or second continuous flow process step may be independently be selected from the group consisting of a plug flow reactor, a tubular flow reactor, a continuous flow reactor, wherein the chemical reactions take place in a confinement with upper lateral dimensions of about ≤5 mm, or of about ≤4 mm, a continuous flow reactor, wherein the chemical reactions take place in a confinement with lateral dimensions of from about ≥0.25 mm up to about ≤5 mm, or of up to about ≤4 mm, preferably of from about ≥0.5 mm up to about ≤5 mm, or of up to about ≤4 mm, and most preferably of from about ≥1 mm up to about ≤5 mm, or of up to about ≤4 mm, and a microreactor.

The invention, employing at least one microreactor, preferably employing at least one SiC-microreactor, provides the advantages in that the processes for the manufacture are industrially feasible, e.g. easily scalable to industrial yields, and in that the process in particular shows improved (e.g. good) selectivity and low energy consumption for the targeted products. Especially, it is an advantage of the present the invention in that it provides an improved and/or optimized process for the manufacture of TFEA, in particular by reacting HCFC-133a as a starting material or intermediate material with HF in the presence of the catalyst. A particular advantage is also that the present the invention provides an improved and/or optimized process for the manufacture of TFEA and/or for the manufacture of HCFC-133a wherein the TFEA and/or the HCFC-133a can be easily, e.g. by a method with only low energy consumption, purified and/or isolated, and wherein preferably the process for purifying and/or isolating does not require a distillation. Advantageously, especially in comparison to a distillation method used in the prior arts, the separation, in particular of HCFC-133a from excess HF (density=0.99 g/cm⁻³) and from the catalyst can easily take place in an energy-saving manner by phase separation. Furthermore, the processes for the manufacture of HCFC-133a (1,1,1-trifluoro-2-chloroethane) and/or of TFEA (trifluoroethylamine) can be efficiently combined in that HCFC-133a (1,1,1-trifluoro-2-chloroethane) produced by the method according the invention by using a microreactor, preferably an SiC-microreactor, may preferably advantageously serve as starting material/and/or intermediate material in the manufacture of TFEA (trifluoroethylamine), preferably also in a microreactor.

Thus, a particular advantage of the method of the invention is a high conversion and/or high selectivity, and especially both, high conversion and high selectivity.

In FIG. 1, an exemplary embodiment of a process scheme for the manufacture of TFEA (trifluoroethylamine) and/or of HCFC-133a (1,1,1-trifluoro-2-chloroethane) is shown. Herein, the HCFC-133a (1,1,1-trifluoro-2-chloroethane) produced from trichloroethylene in the presence of a catalyst (antimony pentafluoride, SbF₅) in a first microreactor can be purified and/or isolated to yield HCFC-133a (1,1,1-trifluoro-2-chloroethane) as the final product; and/or the HCFC-133a (1,1,1-trifluoro-2-chloroethane) produced in a first microreactor, optionally can be purified, and then be used as starting material/and/or intermediate material in the manufacture of TFEA (trifluoroethylamine) in a second microreactor.

The catalyst antimony pentafluoride (SbF₅), in the manufacture of HCFC-133a (1,1,1-trifluoro-2-chloroethane), can be used as such, e.g. prepared prior to reaction in an autoclave by reaction of SbCl₅ with HF, consists of SbF₅ in HF which forms the active species $H_2F^+SbF_6^-$, or may be formed in situ by reacting antimony pentachloride (SbCl₅) with HF. Herein, more than one microreactor, preferably more than one SiC-microreactors, are used in the production, preferably in the industrial production, and these microreactors, preferably these SiC-microreactors, are used in a subsequent arrangement.

Although, FIG. 1 exemplifies the use of two microreactors, of course as described above, the first and/or second reactor independently can be a microreactor in combination with a continuous flow reactor with upper lateral dimensions as defined above, or can also be continuous flow reactor with upper lateral dimensions as defined above, without employing a microreactor, e.g. independently a plug flow reactor with upper lateral dimensions and/or tubular flow reactor, each with upper lateral dimensions as defined above.

In the FIG. 1, the term "cat" means "catalyst" especially a halogenation catalyst, more particularly a fluorination catalyst; the term "TRI" means trichloroethylene ($Cl_2C=CHCl$).

In this exemplary embodiment of FIG. 1, the first microreactor suitable for industrial production is, e.g., made of SiC as offered by Dow Corning as Type GI SiC or Chemtrix MR555 Plantrix (5 to 400 kg per hour) or, e.g. of Hastelloy C as offered by Ehrfeld. For the second microreactor, the construction material is SiC only. It is of course possible to use SiC-microreactors twice, e.g. as a first SiC-microreactor, and then subsequently e.g. as a second SiC-microreactor for the manufacture of TFEA (trifluoroethylamine) from HCFC-133a (1,1,1-trifluoro-2-chloroethane) obtained in the first SiC-microreactor. For laboratory search, e.g. on applicable reaction and/or upscaling conditions, for example, as a microreactor the reactor type Plantrix of the company Chemtrix is also suitable as a first and/or as a second microreactor.

The following examples are intended to further illustrate the invention without limiting its scope.

EXAMPLES

Remark to Equipment:
First Trials were Made in a 250 ml Roth Autoclave:

Remark to equipment and material of construction: The liquid phase of the catalyst mixture in organics is extremely corrosive, so if the autoclave is NOT inside SiC or plastics coated, a HDPTFE inliner is the best option. The gas phase during reaction is less corrosive, high grade stainless steel (1.4571) or even better Hastelloy is sufficient—once more, ONLY resistant for gas phase during reaction !! Inside of the autoclase, a simple also plastics coated stir bar on a magnetic stirrer is convenient. A 250 ml Roth autoclave for trials to 200 bar out of 1.4571 (V4A steel=1.4571) is sufficient. The autoclave has a coated rupture disc (bursting disc, 100 bar), deep pipe out of plastics (PTFE) and as said, a HDPTFE inliner replacing the glas tube inliner usually delivered by Roth. Here, as an example, the link is provided for further information:
https://www.carlroth.com/en/en/Labware/Laboratory-appliances/Autoclaves/High-pressure-laboratory-autoclave-Model-II/Basic-equipment/p/0000000000007a0800020023_en As the active catalyst is $SbF_5$ in HF, commercially available $SbF_5$ is first pre-fluorinated.

Example 1

Pre-Fluorination Procedure in Autoclave:

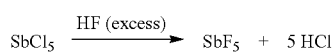

In a 250 ml autocalve (high grade stainless steel 1.4571, Roth company, 1 deep pipe made out of plastics, 1 outlet over gas phase) with HDPTFE Inliner and magnetic stirrer, 36.78 g (0.123 mol) SbCl5 are placed, the autoclave is closed and a 20 fold molar excess of HF (waterfree) (2.46 mol, 49.22 g) is fed from a HF cylinder's liquid phase (cylinder has to be pressurized before with $N_2$) into the autoclave. Even if pressure in the autoclave raises already immediately through the formed HCl in the autoclave after contact with HF, the autoclave is stirred with said magnetic stirrer and heated in an oil bath or electrical heater for 3 h to 100° C. to get an almost complete exchange of Chlorine atoms by fluorine atoms. The pressure on the autoclave is very carefully OVER THE GAS PHASE exit of the autoclave released after cooling down of the autoclave to room temperature to atmospheric pressure into a (just water containing) scrubber (the scrubber must be made out of plastics !), the autoclave is kept closed ! There should be a safety walve (check valve, one way valve) between scrubber and autoclave so that NO water can come back into autoclave !

Example 2

Fluorination Step in (Batch) Autoclave:

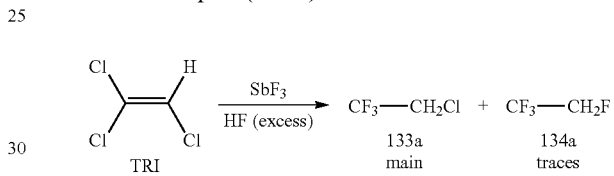

100.0 g (4.998 mol) fresh HF were added into the autoclave over the deep pipe at room temperature, then 62.14 g (0.473 mol) Trichloroethylen (TCE) were dosed with an HPLC pump over the deep pipe into the autoclave (also at room temperature), pressure will start to raise. The autoclave is heated in an oil bath or electrically to 100° C. for 1 h (better 2 h). The pressure will rise constantly. Afterwards, after cooling to room temperature, the pressure is slowly and very carefully released OVER THE GAS PHASE exit of the autoclave to atmospheric pressure into a scrubber with fresh ice water (work up step 1, not with the scrubber water already used for the pre-fluorination), a 2nd phase will be optionally formed already, especially during the end of pressure release. Now the autoclave either is pressurized again over the gas phase inlet of the autoclave with $N_2$ pressure and the remaining content in the autoclave is carefully fed into the scrubber over the deep pipe (liquid phase exit) of the autoclave (work up step 2). Organic phases, always kept cold (preferred in ice or dry ice bath), were combined, neutralized and analyzed by GC and GC-MS. The conversion of TRI was quantitative; the isolated yield in 133a was 97%. Traces of 134a were present too. The experiments were done in extremely good vented hood and full workers protection as boiling point of 133a is very low and as the compound and potential intermediates are very toxic.

Example 3

Continuous Example Connected with Amination Step

Fluorination Step:
TRI was fed out of a storage tank together with HF (molar ration TRI/HF=1:9) containing 10 mol % $SbF_5$ (prepared according to the pre-fluorination procedure in batch) into a ChemtrixMicroreactor (27 ml) made out of SiC heated to 110° C., feed is controlled over a process control system securing a residence time of 200 seconds. A cylon, where a pressure valve is keeping 20 bar pressure, is used after the microreactor to remove some HCl before the mixture goes into a settler to separate organic phase with the 133a and a HF phase containing the catalyst and some HCl. The organic phase is subjected to a pressure distillation to get pure (HF free) 133a. There is a storage (or puffer) tank after the 133a distillation.

Amination Step ($NH_3$ as Cl-Scavenger):

133a is fed together with liquid $NH_3$ into a 2nd microreactor. This reactor can be out of stainless steel or also SiC (volume 27 ml). This reactor is heated to 190° C. before 133a and $NH_3$ feed was started in a molar ratio of 3:1 to obtain $CF_3$—$CH_2NH_2$ together with $NH_4Cl$ dissolved in the product. After final distillation at atmospheric pressure at a transition temperature of 40° C., the obtained yield was 89%.

Amination Step with DMAP as Catalyst/Scavenger:

If 133a is fed together with $NH_3$ and 10 mol-% commercial DMAP (dimethylaminopyridine), the temperature can be lowered to at least 110° C. At this temperature the yield in trifluoroethylamine was 95%. After final distillation at atmospheric pressure at a transition temperature of 39° C., the obtained yield was 94%.

What is claimed is:

1. A process for the manufacture of HCFC-133a (1,1,1-trifluoro-2-chloroethane) in liquid phase consisting of the steps of:
   (a) providing liquid TRI (trichloroethylene) as a starting material;
   (b) providing liquid HF (hydrogen fluoride) and a fluorination promoting catalyst, wherein the fluorination catalyst is selected from the group consisting of Sb fluorination catalysts providing the active species $H_2F^+SbF_6^-$;
   (c) mixing the liquid TRI of (a) with the liquid HF and the said catalyst of (b), and wherein there is not added any additional solvent in the process;
   (d) feeding the liquid phase mixture obtained in (c) into at least one continuous flow reactor with upper lateral dimensions of about ≤5 mm, and therein carrying out the reaction of liquid TRI with liquid HF in the presence of the catalyst to obtain a reaction mixture comprising HCFC-133a;
   (e) withdrawing the reaction mixture obtained in (d) from the microreactor, to yield a after distillation HCFC-133a product;
   (f) purifying and/or isolating the HCFC-133a product obtained in step (e) to yield purified and/or isolated HCFC-133a, and wherein the purifying and/or isolating of HCFC-133a consists of a phase separation method, to yield purified and/or isolated HCFC-133a.

2. The process for the manufacture of HCFC-133a (1,1,1-trifluoro-2-chloroethane) according to claim 1, wherein at least one of the said continuous flow reactors, in step (d) independently is a SiC-continuous flow reactor.

3. The process for the manufacture of HCFC-133a (1,1,1-trifluoro-2-chloroethane) according to claim 1, wherein the at least one of the microreactors in step (d) independently is a SiC-microreactor.

4. The process for the manufacture of HCFC-133a (1,1,1-trifluoro-2-chloroethane) according to claim 1, wherein in the fluorination reaction the halogenation catalyst is antimony pentafluoride ($SbF_5$) and is prepared in an autoclave by $SbF_5$ in HF which forms the active species $H_2F^+SbF_6^-$, prior to reaction step (d).

5. The process for the manufacture of HCFC-133a (1,1,1-trifluoro-2-chloroethane) according to claim 1, wherein the continuous flow reactor is with upper lateral dimensions of about ≤4 mm.

6. The process for the manufacture of HCFC-133a (1,1,1-trifluoro-2-chloroethane) according to claim 1, wherein the continuous flow reactor is a microreactor.

7. The process for the manufacture of HCFC-133a (1,1,1-trifluoro-2-chloroethane) according to claim 1, wherein the continuous flow reactor is a microreactor and the mixture obtained in (c) is fed into the microreactor under one or more of the following conditions:
   flow rate: of from about 10 ml/h up to about 400 l/h;
   temperature: of from about 30° C. up to about 150° C.;
   pressure: of from about 5 bar up to about 50 bar;
   residence time: of from about 1 second up to about 60 minutes.

8. A process according to claim 7, wherein in the step (d) the residence time is from about 1 minute up to about 60 minutes.

* * * * *